US010957454B2

(12) United States Patent
Li et al.

(10) Patent No.: US 10,957,454 B2
(45) Date of Patent: Mar. 23, 2021

(54) DISPLAYING CORONARY ARTERIES (71) Applicant: Neusoft Medical Systems Co., Ltd., Liaoning (CN)

(72) Inventors: Bingsheng Li, Shenyang (CN); Wei He, Shenyang (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 68 days.

(21) Appl. No.: 16/358,449

(22) Filed: Mar. 19, 2019

(65) Prior Publication Data
US 2019/0295731 A1     Sep. 26, 2019

(30) Foreign Application Priority Data

Mar. 23, 2018  (CN) .......................... 201810245202.0

(51) Int. Cl.
*G16H 50/50* (2018.01)
*G06T 7/11* (2017.01)
(Continued)

(52) U.S. Cl.
CPC ......... *G16H 50/50* (2018.01); *A61B 5/02007* (2013.01); *A61B 6/032* (2013.01); *A61B 6/461* (2013.01); *A61B 6/504* (2013.01); *G06T 7/0012* (2013.01); *G06T 7/11* (2017.01); *G06T 19/20* (2013.01); *A61B 6/466* (2013.01); *A61B 6/481* (2013.01); *A61B 6/503* (2013.01); *A61B 2576/023* (2013.01);
(Continued)

(58) Field of Classification Search
None
See application file for complete search history.

(56) References Cited

U.S. PATENT DOCUMENTS

2004/0249270 A1* 12/2004 Kondo ...................... G06T 7/12
600/425
2012/0093388 A1* 4/2012 Masumoto ............ G06T 7/0012
382/134
(Continued)

FOREIGN PATENT DOCUMENTS

CN         102411795 A     4/2012
CN         106023202 A    10/2016

OTHER PUBLICATIONS

Minwen Zheng, et al., "Transluminal attenuation gradient in coronary computed tomography angiography for determining stenosis severity of calcified coronary artery: a primary study with dual-source CT," Eur Radiol (2015) 25:1219-1228.
(Continued)

*Primary Examiner* — Kim Y Vu
*Assistant Examiner* — Nathan J Bloom
(74) *Attorney, Agent, or Firm* — Fish & Richardson P.C.

(57) ABSTRACT

Methods, devices and non-transitory machine readable storage mediums for displaying coronary arteries are provided. In one aspect, a method includes: obtaining a coronary artery model of the coronary arteries, obtaining values of one or more coronary artery parameters of the coronary artery model according to the coronary artery model, determining colors corresponding to the values of the one or more coronary artery parameters, and acquiring a pseudo-color coronary artery model of the coronary arteries by displaying the coronary artery model with the determined colors.

19 Claims, 5 Drawing Sheets

(51) Int. Cl.
    *A61B 5/02*      (2006.01)
    *A61B 6/03*      (2006.01)
    *A61B 6/00*      (2006.01)
    *G06T 7/00*      (2017.01)
    *G06T 19/20*     (2011.01)

(52) U.S. Cl.
    CPC ............ *G06T 2207/10081* (2013.01); *G06T 2207/30048* (2013.01); *G06T 2207/30101* (2013.01); *G06T 2219/2012* (2013.01)

(56) References Cited

U.S. PATENT DOCUMENTS

| | | | | |
|---|---|---|---|---|
| 2013/0066197 A1* | 3/2013 | Pruvot | ............... | A61B 6/504 600/427 |
| 2014/0276036 A1* | 9/2014 | Collins | ............... | A61B 8/0883 600/431 |
| 2014/0378850 A1* | 12/2014 | Plakas | ............... | A61B 5/7275 600/504 |
| 2016/0058407 A1* | 3/2016 | Wakai | ............... | A61B 5/026 382/103 |
| 2016/0358333 A1* | 12/2016 | Lee | ............... | G06T 7/68 |
| 2017/0301096 A1* | 10/2017 | Weese | ............... | G06T 19/00 |
| 2018/0071027 A1* | 3/2018 | Taylor | ............... | A61B 5/1118 |

OTHER PUBLICATIONS

European Patent Office, Extended European Search Report Issued in Application No. 19164280.0, dated Jul. 25, 2019, Germany, 6 pages.

* cited by examiner

DISPLAYING CORONARY ARTERIES

CROSS REFERENCE TO RELATED APPLICATIONS

This application claims priority to Chinese Patent Application No. 201810245202.0, filed on Mar. 23, 2018, the entire content of which is incorporated herein by reference.

BACKGROUND

Coronary artery disease is common cardiovascular disease, and involves the reduction of blood flow to the heart muscle due to build-up of plaque in the arteries of the heart. The incidence rate of coronary artery disease is getting higher and higher. At present, the coronary artery disease is usually clinically diagnosed by examination approaches such as intravascular ultrasound, coronary computed tomography (CT) angiography, and a coronary catheterization. The coronary CT angiography is a non-invasive diagnostic method, and may generate a three-dimensional model of coronary arteries (referred to as a coronary artery model) to display morphology of the coronary artery.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, systems and apparatus for displaying coronary arteries, which enables a user such as a doctor to conveniently diagnose coronary artery disease.

In general, one innovative aspect of the subject matter described in this specification can be embodied in methods of displaying coronary arteries, including: obtaining a coronary artery model of the coronary arteries; obtaining values of one or more coronary artery parameters of the coronary artery model according to the coronary artery model; determining colors corresponding to the values of the one or more coronary artery parameters of the coronary artery model; and acquiring a pseudo-color coronary artery model of the coronary arteries by displaying the coronary artery model with the determined colors.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. For example, the coronary artery parameters include at least one of: an inner contour diameter of coronary arteries, an outer contour diameter of coronary arteries, an inner contour area of coronary arteries, an outer contour area of coronary arteries, a stenosis ratio, a remodeling index, and a transluminal attenuation gradient.

In some cases, obtaining values of one or more coronary artery parameters of the coronary artery model includes: determining a particular value of a stenosis ratio based on a first inner contour diameter of coronary arteries corresponding to a particular point in a center line of the coronary artery model and a second inner contour diameter of coronary arteries corresponding to a point adjacent to the particular point along the center line.

In some cases, obtaining values of one or more coronary artery parameters of the coronary artery model comprises: determining a particular value of a remodeling index based on a first outer contour area of coronary arteries corresponding to a particular point in a center line of the coronary artery model and a second outer contour area of coronary arteries corresponding to a point adjacent to the particular point along the center line.

In some cases, obtaining values of one or more coronary artery parameters of the coronary artery model includes: determining a value of a transluminal attenuation gradient based on a respective mean gray value of each of a plurality of coronary artery sections of the coronary artery model, each of the coronary artery sections corresponding to a respective point along a center line of the coronary artery model.

In some implementations, displaying the coronary artery model with the determined colors includes: displaying the coronary artery model with the determined colors according to one or more display rules selected by a user. The display rules can include: displaying colors in different regions on the coronary artery model according to values of one of the coronary artery parameters in the different regions.

In some cases, the display rules include: displaying colors in different regions on the coronary artery model according to values of two or more different parameters of the coronary artery parameters in the different regions. In some cases, the display rules include: when a value of a particular coronary artery parameter in a particular region on the coronary artery model exceeds a preset threshold of the particular coronary artery parameter, displaying colors in the particular region according to values of the particular coronary artery parameter in the particular region. In some cases, the display rules include one of: displaying an entirety of the coronary artery model and displaying a selected part of the coronary artery model.

In some implementations, determining colors corresponding to the values of the one or more coronary artery parameters includes: determining a color bar according to a value range of a particular coronary artery parameter, where the color bar includes a respective particular color corresponding to each value within the value range of the particular coronary artery parameter; and determining the colors corresponding to the particular coronary artery parameter of the coronary arteries according to the color bar and the values of the particular coronary artery parameter.

Obtaining values of one or more coronary artery parameters of the coronary artery model can include: obtaining first values of the particular coronary artery parameter of first points of the coronary artery model. Determining colors corresponding to the values of the one or more coronary artery parameters can include: determining values of the particular coronary artery parameter of points on a surface of the coronary arteries based on the first values of one or more of the first points that are on the surface; and obtaining colors of the points on the surface by querying the color bar and the values of the particular coronary parameters of the points on the surface.

The first points can be along a center line of the coronary artery model. Each of the first points can correspond to a respective coronary artery section of the coronary arteries, and determining values of the particular coronary artery parameters of points on the surface of the coronary arteries can include: assigning the first values of the first points to be second values of second points on the surface that are on the respective coronary artery sections of the first points; and determining third values of third points on the surface that are not on the respective coronary artery sections of the first points based on the second values of the second points on the surface.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
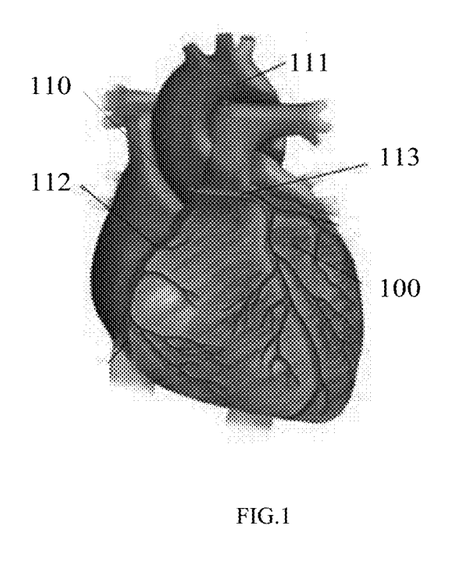
FIG. 1 is a schematic diagram illustrating coronary arteries.

Coronary CT angiography is a non-invasive diagnostic method, and may generate a three-dimensional model of coronary arteries (referred to as a coronary artery model) to display morphology of the coronary artery. As shown in FIG. 1, coronary arteries 110 are arteries that transport blood into and out of a heart 100. The coronary arteries 110 arise from the root of an ascending aorta 111. The coronary arteries 110 are mainly composed of the left coronary artery 112 and the right coronary artery 113, which are located on a surface of the heart 100. In a display of the coronary artery model, the coronary arteries 110 have a luminal feature with relatively high gray values. However, the current coronary artery model only displays the morphology of the coronary arteries, and cannot visually display reference factors (e.g., coronary artery stenosis and myocardial ischemia) for diagnosing coronary artery disease. Therefore, the current display manner of the coronary artery model is inconvenient for a doctor to diagnose coronary artery disease.

Figure 2:
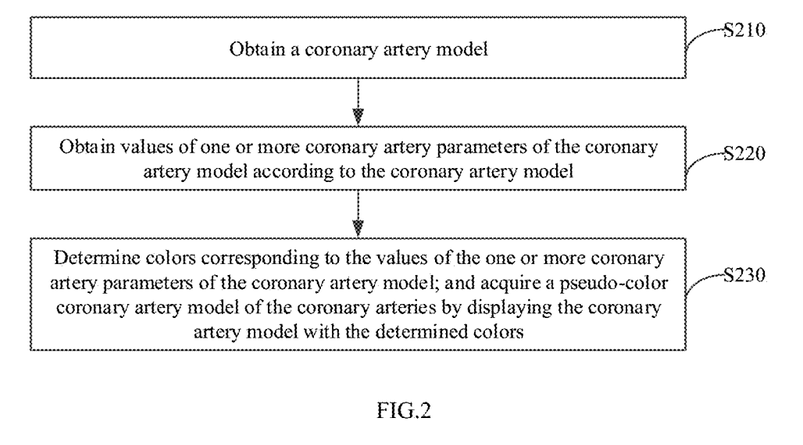
FIG. 2 is a flowchart illustrating a process of a method of displaying coronary arteries according to an example of the present disclosure.

Implementations of the present disclosure provides methods for displaying coronary arteries, which can solve the above issues. FIG. 2 is a flowchart illustrating a process of a method of displaying coronary arteries according to an example of the present disclosure. The method may include the following steps.

At step S210, a coronary artery model is obtained.

At this step, the coronary artery model may be obtained in a number of manners. In an example, a coronary artery model of coronary arteries may be generated based on data from coronary CT angiography. The coronary artery model may be obtained as follows.

Coronary CT angiography may be performed on a patient to obtain a CT image of coronary arteries for the patient.

A coronary artery opening point is calculated based on the CT image. Firstly, a left coronary artery opening point and a right coronary artery opening point are located based on the CT image. In an example, an ascending aorta may be firstly extracted based on the CT image. The ascending aorta may be extracted by a training method or a morphological method (e.g., Hough transform and clustering) which may obtain a tissue boundary of the ascending aorta. Then, outward iteration is performed for a region growth based on the boundary of the obtained ascending aorta. After multiple iterations, a region that is conformed with features of coronary arteries is taken as coronary artery opening points. The left and right coronary artery opening points for most coronary arteries are basically fixed, that is, the right coronary artery opening point is located at the upper left side of the ascending aorta and the left coronary artery opening point is located at the right side of the ascending aorta. Thus, the left and right coronary artery opening points may be distinguished by using the direction information.

A coronary artery model is generated. According to the left and right coronary artery opening points obtained above and the CT image, a coronary artery tissue may be extracted based on a fast marching algorithm. A new coronary artery tissue may be evaluated and track by a variety of tube analysis methods, for example, by a principle component analysis (PCA) method, and the coronary artery tissue may be finally obtained by performing multiple iterations. Then, a tree-shaped center line of the coronary arteries is generated by performing center line extraction for the coronary artery tissue. The center line may be extracted by using methods well known to those skilled in the art. A plurality of center points are taken on the center line based on a particular sampling interval. For each center point, a local coordinate system of the center point is set and the center point is determined as the center of a circle. On an XY plane of the local coordinate system, lines are emitted outward from the center of the circle at a certain angular interval to obtain an inner contour line by adopting a fuzzy similarity determination criterion. An outer contour line is determined by growing the inner contour line outwardly according to information such as gradients of the CT image. For all the center points on the center line, a series of inner/outer contour lines can be calculated as described above. Then a variable model may be formed with the series of inner/outer contour lines. Ideal contours may be obtained by performing iterative evolution with the variable model. A coronary artery model is generated based on the ideal contours.

At step S220, values of one or more coronary artery parameters of the coronary artery model are obtained according to the coronary artery model.

The coronary artery model mentioned in examples of the present disclosure may include an inner contour of the coronary artery model and an outer contour of the coronary artery model.

At this step, values of one or more coronary artery parameters of the coronary artery model may be calculated according to the above coronary artery model. The coronary artery parameters may include an inner contour diameter of coronary arteries, an outer contour diameter of coronary arteries, an inner contour area of coronary arteries, an outer contour area of coronary arteries, a stenosis ratio, a remodeling index (RI), and a transluminal attenuation gradient (TAG). The methods of calculating the above coronary artery parameters will be described below.

1. The inner contour diameter of coronary arteries (d): an inner contour diameter of coronary arteries corresponding to any point in the center line may be obtained according to the center line and the inner contour of the coronary artery model.

2. The outer contour diameter of coronary arteries (D): the outer contour diameter of coronary arteries corresponding to any point in the center line may be obtained according to the center line and the outer contour of the coronary artery model.

3. The inner contour area of coronary arteries (s): an inner contour area of coronary arteries corresponding to a certain point in the center line of the coronary artery model may be obtained according to the inner contour diameter corresponding to the certain point.

4. The outer contour area of coronary arteries (S): an outer contour area of coronary arteries corresponding to a certain point in the center line of the coronary artery model may be obtained according to the outer contour diameter corresponding to the certain point.

5. The stenosis ratio: coronary artery stenosis may be caused by atherosclerosis. Stenosis may lead to myocardial ischemia and cause coronary artery disease when reaching a certain degree. Thus, the stenosis ratio of coronary arteries is an important parameter for diagnosing coronary artery disease. The stenosis ratio may be obtained based on an inner contour diameter of coronary arteries corresponding to a certain point in the center line of the coronary artery model and an inner contour diameter of coronary arteries corresponding to a point adjacent to the certain point along the center line. In an example, the stenosis ratio may be calculated based on an inner contour diameter corresponding to a lesion point and an average inner contour diameter corresponding to proximal reference points along the center line.

At this step, stenosis ratios may be calculated for all points in the center line of the coronary artery model. For a certain point, points with a certain distance away from the certain point may be taken as proximal reference points. One proximal reference point may be in the left side of the certain point, and another proximal reference point may be in the right side of the certain point. For example, the certain distance may be 1 centimeter (cm). An inner contour diameter $d_0$ at the certain point is obtained, and inner contour diameters $d_1$ and $d_2$ at the proximal reference points are also obtained respectively. An average inner contour diameter at the reference points is $(d_1+d_2)/2$. In this way, a stenosis ratio value $f_{SR}$ for the certain point may be calculated based on formula (1) as shown in below:

$$f_{SR}=2\times d_0/(d_1+d_2) \tag{1}$$

The stenosis ratio values for all points in the center line of the coronary artery model may be automatically calculated based on the formula (1), thereby obtaining a list of stenosis ratio values for the coronary artery model.

6. The RI: the RI may be a ratio of an outer contour area of coronary arteries corresponding to a plaque lesion point to an outer contour area of coronary arteries corresponding to a point adjacent to the plaque lesion point along the center line. If the RI is greater than 1, the plaque lesion may be referred as positive remodeling. If the RI is less than 1, the plaque lesion may be referred as negative remodeling. Mild to moderate coronary artery stenosis can be mostly caused by positive remodeling, and the plaques are easy to rupture. Therefore, the RI of coronary arteries provides an important basis for a doctor to distinguish the nature of plaques.

At this step, the RI may be calculated based on an outer contour area corresponding to a certain point in the center line of the coronary artery model and an average outer contour area corresponding to proximal reference points along the center line.

In an example, the RIs are calculated may be calculated for all points in the center line of the coronary artery model. For a certain point, points with a certain distance away from the certain point may be taken as proximal reference points. One proximal reference point may be in the left side of the certain point, and another proximal reference point may be in the right side of the certain point. For example, the certain distance may be 1 cm. An outer contour area $S_0$ at the certain point is obtained, and outer contour areas $S_1$ and $S_2$ at the proximal reference points are also obtained respectively. An average outer contour area at the reference points is $(S_1+S_2)/2$. In this way, a RI value $f_{RI}$ for the certain point may be calculated based on formula (2) as shown in below:

$$f_{RI}=2\times S_0/(S_1+S_2) \tag{2}$$

The RI values for all points in the center line of the coronary artery model may be automatically calculated based on the formula (2), thereby obtaining a list of RI values for the coronary artery model.

7. The TAG: the TAG may be defined as a linear regression coefficient between luminal attenuation and axial distance, that is, the luminal radiological contrast attenuation (e.g., Hounsfield units [HU]) is measured at a unit length interval along the coronary arteries from the coronary artery opening point. For example, the unit length interval may be 10 millimeter (mm). The TAG may reflect blood flow in coronary arteries. TAG value may drop rapidly when coronary artery stenosis is severe. Therefore, the TAG may improve diagnostic accuracy, especially for diagnosing coronary artery calcification.

At this step, the transluminal attenuation gradient (TAG) is calculated based on a mean gray value of each of a plurality of coronary artery sections, where each of the coronary artery section corresponds to a point along the center line of the coronary artery model.

In an example, a plurality of points may be obtained at a unit length interval along the center line of the coronary artery model from the coronary artery opening point. For example, the unit length interval may be 10 mm. For each of the points, a mean gray value of a coronary artery section may be measured, and the mean gray value may reflect the luminal radiological contrast attenuation at the point. Then, a plurality of mean gray values may be obtained for the whole coronary artery model. A TAG curve may be generated according to a plurality of the distances from the coronary artery opening point to the plurality of points and the corresponding mean gray values at the plurality of points. A linear regression coefficient may be then obtained based on the TAG curve. Finally, TAG value may be obtained based on the linear regression coefficient.

It is to be noted that the above certain distances (1 cm) and unit length interval (10 mm) used for calculating the stenosis ratio, the RI, and the TAG are all exemplary, and may be adjusted according to an actual situation, which are not limited herein.

At step S230, colors corresponding to the values of the one or more coronary artery parameters are determined, and a pseudo-color coronary artery model of the coronary arteries is acquired by displaying the coronary artery model with the determined colors.

In an example, the coronary artery model may be divided into a number of meshes by a finite element analysis method. That is, a coronary artery surface (e.g., an inner contour of the coronary artery model or an outer contour of the coronary artery model) in the coronary artery model may be divided into multiple triangle meshes, quadrilateral meshes or polygonal meshes. For a certain coronary artery parameter, a corresponding color bar is used to represent a relationship between values of the certain coronary artery parameter and colors. The color bar includes colors corresponding to each value within a value range of the coronary artery parameter. The maximum value and the minimum value of the certain coronary artery parameter may determine the color at both ends of the color bar. Next, for each point within each mesh which composed the coronary artery model, value of the particular parameter is calculated by an endpoint interpolation method.

Figure 2A:
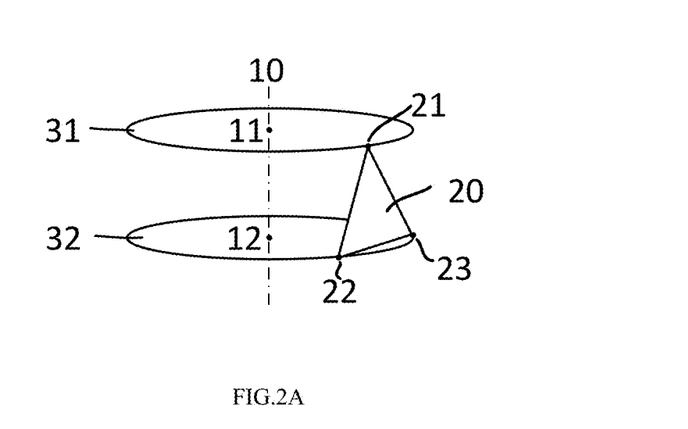
FIG. 2A is a schematic diagram illustrating how to calculate coronary arterial parameter values in a surface of a coronary artery model according to an example of the present disclosure.

As shown in FIG. 2A, for example, the surface of the coronary arteries is formed by a plurality of triangle meshes. One triangle mesh 20 has three endpoints 21, 22 and 23. At step S210, a center line 10 may be obtained. A certain coronary artery parameter value of points 11 and 12 in the center line 10 may be calculated at step S220. Since the point 11 and the endpoint 21 are on the same coronary artery section 31, the certain parameter value at the point 11 may be assigned to the endpoint 21. Since the point 12 and the endpoint 22 and 23 are on the same coronary artery section 32, the certain parameter value at the point 12 may be assigned to the endpoint 22 and 23. Then, the certain parameter value of each point within the triangle mesh 20 may be calculated by the endpoint interpolation method according to the certain parameter values at the endpoints 21, 22 and 23.

A color at a point may be obtained by querying the color bar according to a parameter value at the point. For example, an inner contour diameter of coronary arteries is 1 mm at a point, after querying the color bar, the color corresponding to the point may be dark red. An inner contour diameter of coronary arteries is 2 mm at another point, after querying the color bar, the color corresponding to the point is light blue. Colors of the coronary artery model may be determined by a pseudo-color surface drawing method. Then, a pseudo-color coronary artery model may be acquired by displaying the coronary artery model with the determined colors.

In some examples, different colors may be displayed in different regions of the pseudo-color coronary artery model according to one or more of a plurality of displaying rules. The plurality of display rules may include the followings.

In the first rule, colors to be displayed in different regions on the coronary artery model are determined according to a single coronary artery parameter.

Figure 3:
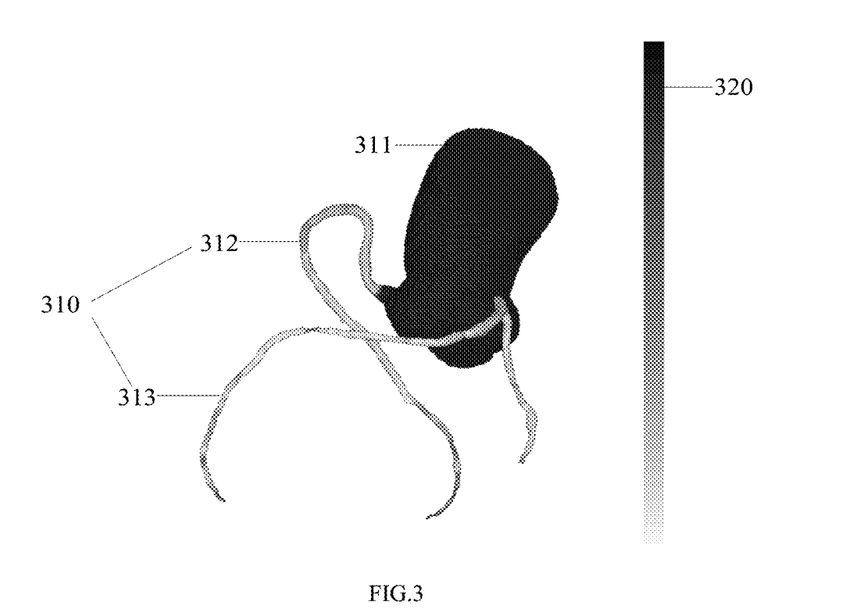
FIG. 3 is a schematic diagram illustrating a pseudo-color coronary artery model displaying a parameter of stenosis ratio according to an example of the present disclosure.

As shown in FIG. 3, a pseudo-color coronary artery model 310 displays a left coronary artery 312 and a right coronary artery 313, which both arise from an ascending aorta 311. In FIG. 3, a color bar 320 is used to represent a relationship between the stenosis ratio and the color. A color to be displayed in each region on the pseudo-color coronary artery model 310 is determined according to a value of the stenosis ratio for the region. Certainly, other coronary artery parameters may also be displayed in the manner of FIG. 3 in addition to the stenosis ratio.

In the second rule, colors to be displayed in different regions on the coronary artery model are determined according to different coronary artery parameters.

Figure 4A:
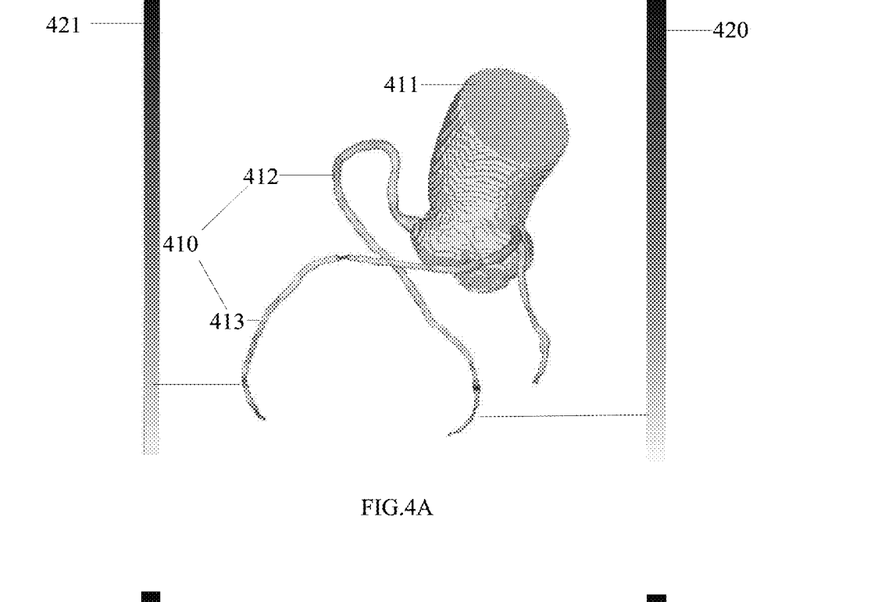
FIG. 4A is a schematic diagram illustrating a pseudo-color coronary artery model according to another example of the present disclosure.

In an example, as shown in FIG. 4A, a pseudo-color coronary artery model 410 displays a left coronary artery 412 and a right coronary artery 413, which both arise from an ascending aorta 411. A color to be displayed in each region on the left coronary artery 412 is determined according to a value of a stenosis ratio for the region, and a color to be displayed in each region on the right coronary artery 413 is determined according to a value of a RI of the region. In FIG. 4A, a color bar 420 is used to represent a relationship between the stenosis ratio and the color, and a color bar 421 is used to represent a relationship between the RI and the color. Certainly, it may be understood that the color of any region on the pseudo-color coronary artery model may be determined according to one coronary artery parameter, and the colors of any other region may be determined according to any other coronary artery parameter.

In the third rule, when a value of a particular coronary artery parameter in a particular region on the pseudo-color coronary artery model exceeds a preset threshold of the coronary artery parameter, the region is taken as a lesion region, and a color to be displayed in the lesion region is determined according to the value of the particular coronary artery parameter.

Figure 4B:
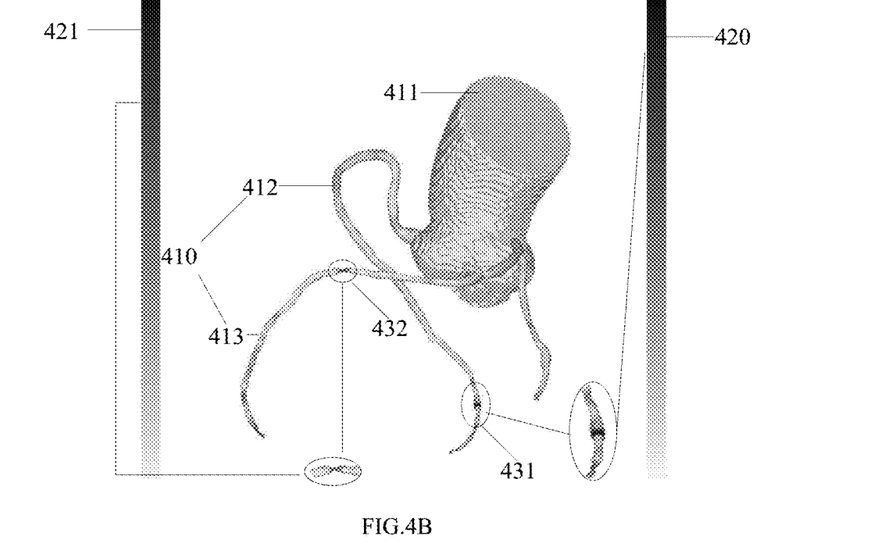
FIG. 4B is a schematic diagram illustrating a pseudo-color coronary artery model according to still another example of the present disclosure.

In a practical application, a doctor mostly focuses on a lesion position of coronary arteries. In some examples, after values of a particular coronary artery parameter of each region of the coronary artery model is obtained by calculation, the values may be compared with a preset threshold of the particular coronary artery parameter. If a value of the coronary artery parameter of a particular region exceeds the preset threshold, for example, a stenosis ratio value in a region 1 exceeds a preset threshold of the stenosis ratio and a RI value in a region 2 exceeds a preset threshold of the RI, the color to be displayed in the region 1 may be determined according to the stenosis ratio value and the color to be displayed in the region 2 may be determined according to the RI value. As shown in FIG. 4B, a pseudo-color coronary artery model 410 displays the left coronary artery 412 and the right coronary artery 413, which both arise from the ascending aorta 411. A value of the RI in a region 431 on the left coronary artery 412 exceeds a preset threshold of the RI, and a value of the stenosis ratio in a region 432 on the right coronary artery 413 exceeds a preset threshold of the stenosis ratio. The region 431 and 432 may be taken as lesion regions. In FIG. 4B, the color of the region 431 is determined according to the value of the RI, and the color of the region 432 is determined according to the value of the stenosis ratio. The color bar 420 is used to represent a relationship between the RI and the color, and the color bar 421 is used to represent a relationship between the stenosis ratio and the color. In FIG. 4B, in addition to the region 431 and the region 432, regions on the coronary artery model may be displayed according to values of the RI or values of the stenosis ratio. In addition, regions other than a lesion region may also be displayed with a same color to highlight the lesion region corresponding to a coronary artery parameter. By using this rule, a doctor may rapidly see the lesion position of the coronary arteries, thereby bringing convenience to disease diagnosis.

In the fourth rule, the entire coronary artery model is displayed.

Figure 5:
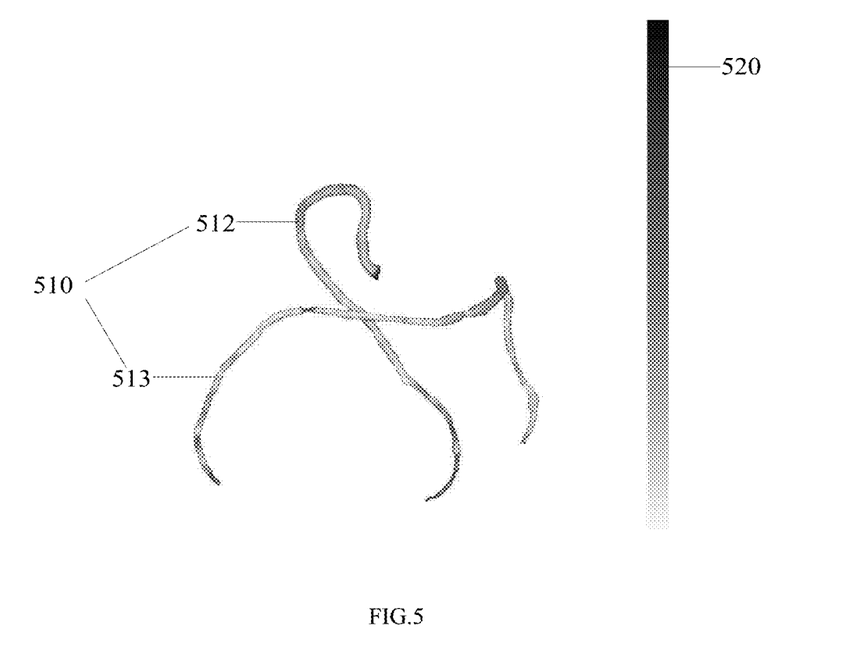
FIG. 5 is a schematic diagram illustrating a pseudo-color coronary artery model displaying entire coronary arteries without an ascending aorta according to an example of the present disclosure.

In some examples, the entire coronary artery model may be displayed. A display result of the pseudo-color coronary artery model may be set based on the fourth rule combined with one or more of the first to third rules. An ascending aorta may be displayed or may not be displayed in the entire pseudo-color coronary artery model. As shown in FIG. 5, an entire pseudo-color coronary artery model 510 displays a left coronary artery 512 and a right coronary artery 513. In FIG. 5, a color bar 520 is used to represent a relationship between the stenosis ratio and the color. The ascending aorta is not displayed in FIG. 5.

In the fifth rule, a part of the coronary artery model is displayed.

Figure 6:
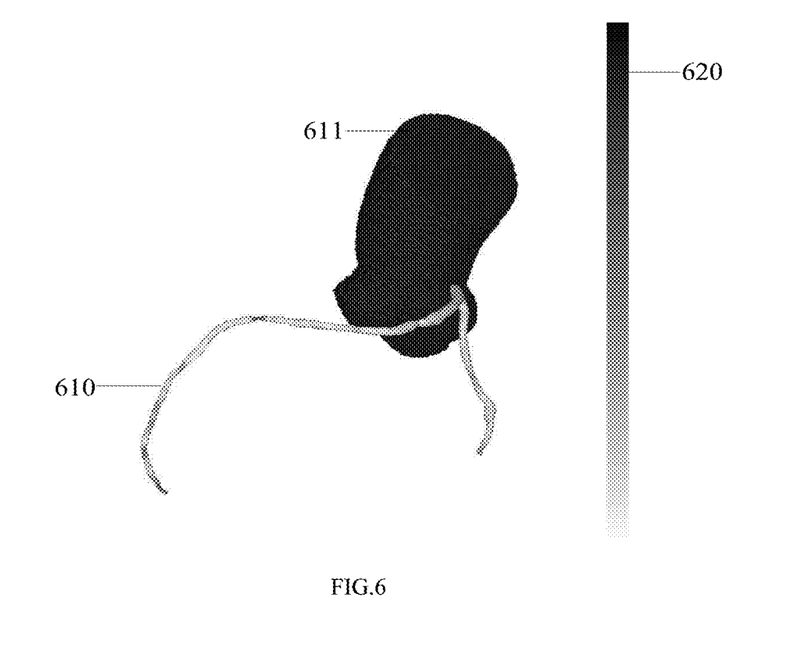
FIG. 6 is a schematic diagram illustrating a pseudo-color coronary artery model displaying right coronary artery only according to an example of the present disclosure.

In some examples, only a part of the coronary artery model may be displayed, for example, only the left coronary artery or only the right coronary artery is displayed. A display result of a pseudo-color coronary artery model may also be set based on the fifth rule combined with one or more of the first to third rules. Similarly, the partial model may also display with an ascending aorta or may not display with an ascending aorta. Displaying only the right coronary artery is taken as an example. As shown in FIG. 6, only the right coronary artery 610 of the pseudo-color coronary artery model is displayed, and the right coronary artery 610 arises from an ascending aorta 611. A color bar 620 is used to represent a relationship between the stenosis ratio and the color. The displaying partial coronary artery model may be the left coronary artery, the right coronary artery, or any region on the coronary artery model.

In some examples, when a user (e.g., a doctor) triggers a selection instruction, the instruction may carry display rule information, for example, the above first to fifth rules. A pseudo-color coronary artery model may be displayed according to the selected display rules. A pseudo-color coronary artery model may also be displayed on a CT device in response to the selection instruction of the user.

In the present disclosure, a coronary artery model of coronary arteries is firstly obtained. Then, one or more coronary artery parameter of the coronary artery model is obtained according to the coronary artery model. Finally, colors corresponding to the one or more coronary artery parameters are determined, and a pseudo-color coronary artery model of the coronary arteries is acquired by displaying the coronary artery model with the determined colors. Since coronary artery parameters of the pseudo-color coronary artery model are visually displayed, a doctor or a patient can clearly see situations of the coronary arteries. For example, a relationship between coronary artery parameters, e.g., the stenosis ratio, the RI and the TAG, and the coronary arteries can be clearly displayed, thereby helping a doctor to rapidly diagnose coronary artery disease.

Based on the method of displaying coronary arteries, a device for displaying coronary arteries is also provided by an example of the present disclosure, which will be detailed below in combination with accompanying drawings.

Figure 7:
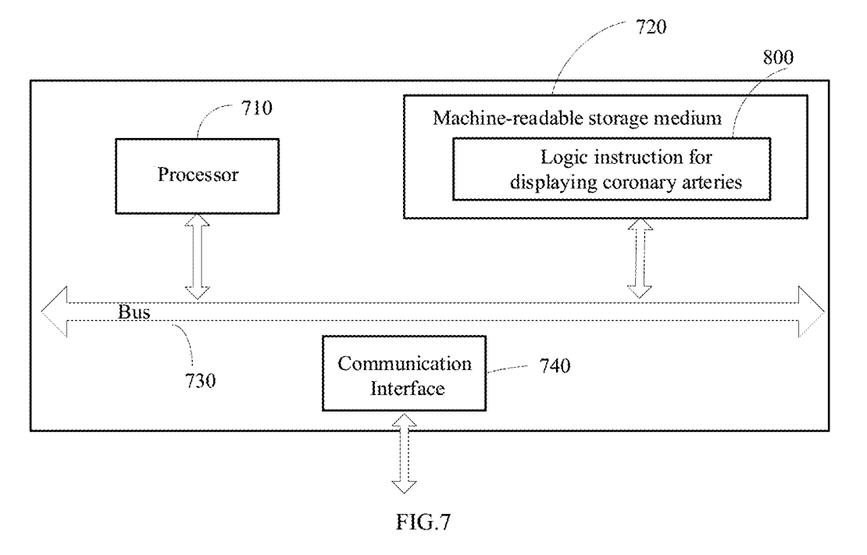
FIG. 7 is a schematic diagram illustrating a hardware structure of a device for displaying coronary arteries according to an example of the present disclosure.

FIG. 7 is a schematic diagram illustrating a hardware structure of a device for displaying coronary arteries according to an example of the present disclosure. The device for displaying coronary arteries may include at least one processor 710 and at least one machine readable storage medium 720, where the processor 710 and the machine readable storage medium 720 are usually connected with each other via an internal bus 730. In other possible implementations, the apparatus may also include an external interface 740 to communicate with other devices or components.

In different examples, the machine readable storage medium 720 is a non-transitory memory. For example, a flash memory, a storage drive (e.g. hard disk drive), a solid state disk, any type of storage disk (e.g., compact disk, Digital Video Disk (DVD)), or a similar storage medium, or a combination thereof. The machine readable storage medium 720 may also include different transitory memories such as Random Access Memory (RAM) to cooperate with the non-volatile memory and the processor.

Figure 8:
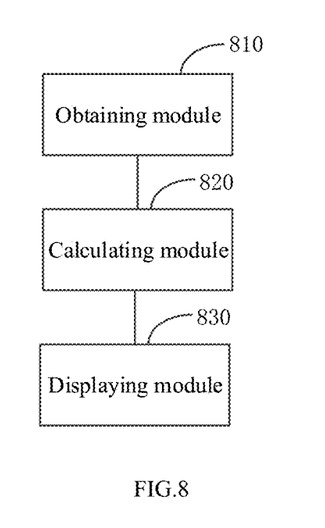
FIG. 8 is a structural diagram illustrating function modules of logic instructions for displaying coronary arteries according to an example of the present disclosure.

Further, the machine readable storage medium 720 stores logic instructions 800 for displaying coronary arteries. As shown in FIG. 8, functionally, the logic instructions may include an obtaining module 810, a calculation module 820 and a displaying module 830.

The obtaining module 810 is configured to obtain a coronary artery model of the coronary arteries.

The calculation module 820 is configured to obtain one or more coronary artery parameters of the coronary artery model according to the coronary artery model.

The displaying module 830 is configured to determining colors corresponding to the one or more coronary artery parameters; and acquire a pseudo-color coronary artery model of the coronary arteries by displaying the coronary artery model with the determined colors.

A software implementation is taken as an example below to further describe how the device for displaying coronary arteries executes the logic instruction 800. In this example, the logic instructions 800 should be understood as a machine executable instruction stored in the machine readable storage medium 720. When a processor 710 of the device in the present disclosure executes the logic instructions 800, the processor 710 performs the following operations by invoking the logic instruction 800 stored in the machine readable storage medium 720.

A coronary artery model of the coronary arteries is obtained.

One or more coronary artery parameters of the coronary artery model are obtained according to the coronary artery model.

Colors corresponding to the one or more coronary artery parameters are determined.

A pseudo-color coronary artery model of the coronary arteries is acquired by displaying the coronary artery model with the determined colors.

In one implementation, the coronary artery parameters include at least one of an inner contour diameter of coronary arteries, an outer contour diameter of coronary arteries, an inner contour area of coronary arteries, an outer contour area of coronary arteries, a stenosis ratio, a remodeling index, and a transluminal attenuation gradient.

Further, the stenosis ratio is obtained based on an inner contour diameter of coronary arteries at a certain point of the coronary artery model and an inner contour diameter of coronary arteries at a point adjacent to the certain point. The remodeling index is obtained by based on an outer contour area of coronary arteries at a certain point of the coronary artery model and an outer contour area of coronary arteries at a point adjacent to the certain point. And the transluminal attenuation gradient is determined based on a mean gray value of each of a plurality of coronary artery sections, where each of the coronary artery sections corresponds to a point along the coronary artery model.

In one implementation, displaying the coronary artery model with the determined colors includes: displaying the coronary artery model with the determined colors according to one or more display rules selected by a user.

Further, the display rules include: determining colors to be displayed in different regions on the coronary artery model according to one coronary artery parameter; determining colors to be displayed in different regions on the coronary artery model according to different coronary artery parameters; when a value of a particular coronary artery parameter in a particular region on the coronary artery model exceeds a preset threshold of the coronary artery parameter, determining the color to be displayed in the region according to the value of the coronary artery parameter; displaying the entire coronary artery model; and displaying a part of the coronary artery model.

In one implementation, determining colors corresponding to the coronary artery parameter includes: determining a color bar according to a value range of the coronary artery parameter, where the color bar includes colors corresponding to each value within the value range of the coronary artery parameter; and determining the colors corresponding to the coronary artery parameter according to the color bar and the value of the coronary artery parameter.

According to a device provided by an example of the present disclosure, coronary artery parameters of the pseudo-color coronary artery model are visually displayed, a doctor or a patient can clearly see situations of coronary arteries. For example, a relationship between coronary artery parameters and the coronary arteries can be clearly displayed, thereby helping a doctor to rapidly diagnose coronary artery disease.

An example of the present disclosure also provides a non-transitory machine readable storage medium for displaying coronary arteries. The machine readable storage medium stores machine-executable instructions where the machine-executable instructions are executed to perform following operations.

A coronary artery model of the coronary arteries is obtained.

One or more coronary artery parameters of the coronary artery model are obtained according to the coronary artery model.

Colors corresponding to the one or more coronary artery parameters are determined.

A pseudo-color coronary artery model of the coronary arteries is acquired by displaying the coronary artery model with the determined colors.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. A method of displaying coronary arteries, comprising:
   obtaining a coronary artery model of the coronary arteries;
   obtaining values of one or more coronary artery parameters of the coronary artery model according to the coronary artery model;
   determining colors corresponding to the values of the one or more coronary artery parameters of the coronary artery model; and
   acquiring a pseudo-color coronary artery model of the coronary arteries by displaying the coronary artery model with the determined colors,
   wherein determining colors corresponding to the values of the one or more coronary artery parameters comprises:
      determining a color bar according to a value range of a particular coronary artery parameter, wherein the color bar comprises a respective particular color corresponding to each value within the value range of the particular coronary artery parameter; and
      determining the colors corresponding to the particular coronary artery parameter of the coronary arteries according to the color bar and the values of the particular coronary artery parameter,
   wherein obtaining values of one or more coronary artery parameters of the coronary artery model comprises:
      obtaining first values of the particular coronary artery parameter of first points of the coronary artery model,
   wherein determining colors corresponding to the values of the one or more coronary artery parameters comprises:
      determining values of the particular coronary artery parameter of points on a surface of the coronary arteries based on the first values of one or more of the first points that are on the surface; and obtaining colors of the points on the surface by querying the color bar and the values of the particular coronary parameters of the points on the surface, wherein the first points are along a center line of the coronary artery model, and each of the first points corresponds to a respective coronary artery section of the coronary arteries, and wherein determining values of the particular coronary artery parameters of points on the surface of the coronary arteries comprises:

assigning the first values of the first points to be second values of second points on the surface that are on the respective coronary artery sections of the first points; and determining third values of third points, that are on the surface of the coronary arteries but not on the respective coronary artery sections of the first points, based on the second values of the second points that are on the surface of the coronary arteries and on the respective coronary artery sections of the first points.

2. The method of claim 1, wherein the coronary artery parameters comprise at least one of:
an inner contour diameter of coronary arteries,
an outer contour diameter of coronary arteries,
an inner contour area of coronary arteries,
an outer contour area of coronary arteries,
a stenosis ratio,
a remodeling index, and
a transluminal attenuation gradient.

3. The method of claim 1, wherein obtaining values of one or more coronary artery parameters of the coronary artery model comprises:
determining a particular value of a stenosis ratio based on a first inner contour diameter of coronary arteries corresponding to a particular point in a center line of the coronary artery model and a second inner contour diameter of coronary arteries corresponding to a point adjacent to the particular point along the center line.

4. The method of claim 1, wherein obtaining values of one or more coronary artery parameters of the coronary artery model comprises:
determining a particular value of a remodeling index based on a first outer contour area of coronary arteries corresponding to a particular point in a center line of the coronary artery model and a second outer contour area of coronary arteries corresponding to a point adjacent to the particular point along the center line.

5. The method of claim 1, wherein obtaining values of one or more coronary artery parameters of the coronary artery model comprises:
determining a value of a transluminal attenuation gradient based on a respective mean gray value of each of a plurality of coronary artery sections of the coronary artery model,
wherein each of the coronary artery sections corresponds to a respective point along a center line of the coronary artery model.

6. The method of claim 1, wherein displaying the coronary artery model with the determined colors comprises:
displaying the coronary artery model with the determined colors according to one or more display rules selected by a user.

7. The method of claim 6, wherein the display rules comprise:
displaying colors in different regions on the coronary artery model according to values of one of the coronary artery parameters in the different regions.

8. The method of claim 6, wherein the display rules comprise:
displaying colors in different regions on the coronary artery model according to values of two or more different parameters of the coronary artery parameters in the different regions.

9. The method of claim 6, wherein the display rules comprise:
when a value of the particular coronary artery parameter in a particular region on the coronary artery model exceeds a preset threshold of the particular coronary artery parameter, displaying colors in the particular region according to values of the particular coronary artery parameter in the particular region.

10. The method of claim 6, wherein the display rules comprise one of:
displaying an entirety of the coronary artery model, and
displaying a selected part of the coronary artery model.

11. A device for displaying coronary arteries, comprising:
at least one processor; and
at least one non-transitory machine readable storage medium coupled to the at least one processor having machine-executable instructions stored thereon that, when executed by the at least one processor, cause the at least one processor to perform operations comprising:
obtaining a coronary artery model of the coronary arteries;
obtaining values of one or more coronary artery parameters of the coronary artery model according to the coronary artery model;
determining colors corresponding to the values of the one or more coronary artery parameters; and
acquiring a pseudo-color coronary artery model of the coronary arteries by displaying the coronary artery model with the determined colors,
wherein determining colors corresponding to the values of the one or more coronary artery parameters comprises:
determining a color bar according to a value range of a particular coronary artery parameter, wherein the color bar comprises a respective particular color corresponding to each value within the value range of the particular coronary artery parameter; and
determining the colors corresponding to the particular coronary artery parameter of the coronary arteries according to the color bar and the values of the particular coronary artery parameter,
wherein obtaining values of one or more coronary artery parameters of the coronary artery model comprises:
obtaining first values of the particular coronary artery parameter of first points of the coronary artery model,
wherein determining colors corresponding to the values of the one or more coronary artery parameters comprises:
determining values of the particular coronary artery parameter of points on a surface of the coronary arteries based on the first values of one or more of the first points that are on the surface; and obtaining colors of the points on the surface by querying the color bar and the values of the particular coronary parameters of the points on the surface, wherein the first points are along a center line of the coronary artery model, and each of the first points corresponds to a respective coronary artery section of the coronary arteries, and wherein determining values of the particular coronary artery parameters of points on the surface of the coronary arteries comprises:

assigning the first values of the first points to be second values of second points on the surface that are on the respective coronary artery sections of the first points; and determining third values of third points, that are on the surface of the coronary arteries but not on the respective coronary artery sections of the first points, based on the second values of the second points that are on the surface of the coronary arteries and on the respective coronary artery sections of the first points.

12. The device of claim 11, wherein the coronary artery parameters comprise at least one of:
an inner contour diameter of coronary arteries,
an outer contour diameter of coronary arteries,
an inner contour area of coronary arteries,
an outer contour area of coronary arteries,
a stenosis ratio,
a remodeling index, and
a transluminal attenuation gradient.

13. The device of claim 12, wherein the stenosis ratio is defined as a ratio between an inner contour diameter of coronary arteries corresponding to a first point in a center line of the coronary artery model and an inner contour diameter of coronary arteries corresponding to a point adjacent to the first point along the center line, wherein the remodeling index is defined as a ratio between an outer contour area of coronary arteries corresponding to a second point in the center line of the coronary artery model and an outer contour area of coronary arteries corresponding to a point adjacent to the second point along the center line, and wherein the transluminal attenuation gradient is defined based on mean gray values of a plurality of coronary artery sections of the coronary artery model, wherein each of the coronary artery sections corresponds to a respective point in the center line along the coronary artery model.

14. The device of claim 11, wherein displaying the coronary artery model with the determined colors comprises:
displaying the coronary artery model with the determined colors according to one or more of a plurality of display rules selected by a user.

15. The device of claim 14, wherein the plurality of display rules comprises:
displaying colors in different regions on the coronary artery model according to a single one coronary artery parameter,
displaying colors in different regions on the coronary artery model according to two or more different coronary artery parameters,
when a value of the particular coronary artery parameter in a particular region on the coronary artery model exceeds a preset threshold of the coronary artery parameter, displaying colors in the particular region according to values of the particular coronary artery parameter in the particular region,
displaying an entirety of the coronary artery model, and
displaying a part of the coronary artery model.

16. A non-transitory machine readable storage medium storing machine-executable instructions, wherein the machine-executable instructions are executed to perform operations comprising:
obtaining a coronary artery model of the coronary arteries;
obtaining values of one or more coronary artery parameters of the coronary artery model according to the coronary artery model;
determining colors corresponding to the values of the one or more coronary artery parameters of the coronary artery model; and
acquiring a pseudo-color coronary artery model of the coronary arteries by displaying the coronary artery model with the determined colors, wherein determining colors corresponding to the values of the one or more coronary artery parameters comprises:
determining a color bar according to a value range of a particular coronary artery parameter, wherein the color bar comprises a respective particular color corresponding to each value within the value range of the particular coronary artery parameter; and
determining the colors corresponding to the particular coronary artery parameter of the coronary arteries according to the color bar and the values of the particular coronary artery parameter, wherein obtaining values of one or more coronary artery parameters of the coronary artery model comprises:
obtaining first values of the particular coronary artery parameter of first points of the coronary artery model, wherein determining colors corresponding to the values of the one or more coronary artery parameters comprises:
determining values of the particular coronary artery parameter of points on a surface of the coronary arteries based on the first values of one or more of the first points that are on the surface; and
obtaining colors of the points on the surface by querying the color bar and the values of the particular coronary parameters of the points on the surface, wherein the first points are along a center line of the coronary artery model, and each of the first points corresponds to a respective coronary artery section of the coronary arteries, and wherein determining values of the particular coronary artery parameters of points on the surface of the coronary arteries comprises:
assigning the first values of the first points to be second values of second points on the surface that are on the respective coronary artery sections of the first points; and
determining third values of third points, that are on the surface of the coronary arteries but not on the respective coronary artery sections of the first points, based on the second values of the second points that are on the surface of the coronary arteries and on the respective coronary artery sections of the first points.

17. The method of claim 1, wherein determining third values of third points, that are on the surface of the coronary arteries but not on the respective coronary artery sections of the first points, based on the second values of the second points that are on the surface of the coronary arteries and on the respective coronary artery sections of the first points comprises:

determining, by endpoint interpolation, the third values of the third points, that are on the surface of the coronary arteries but not on the respective coronary artery sections of the first points, based on the second values of the second points that are on the surface of the coronary arteries and on the respective coronary artery sections of the first points.

18. The device of claim 11, wherein determining third values of third points, that are on the surface of the coronary arteries but not on the respective coronary artery sections of the first points, based on the second values of the second points that are on the surface of the coronary arteries and on the respective coronary artery sections of the first points comprises:

determining, by endpoint interpolation, the third values of the third points, that are on the surface of the coronary arteries but not on the respective coronary artery sections of the first points, based on the second values of the second points that are on the surface of the coronary arteries and on the respective coronary artery sections of the first points.

19. The non-transitory machine readable storage medium of claim 16, wherein determining third values of third points, that are on the surface of the coronary arteries but not on the respective coronary artery sections of the first points, based on the second values of the second points that are on the surface of the coronary arteries and on the respective coronary artery sections of the first points comprises:

determining, by endpoint interpolation, the third values of the third points, that are on the surface of the coronary arteries but not on the respective coronary artery sections of the first points, based on the second values of the second points that are on the surface of the coronary arteries and on the respective coronary artery sections of the first points.

* * * * *